United States Patent
Gustavsson et al.

(10) Patent No.: US 7,323,615 B2
(45) Date of Patent: Jan. 29, 2008

(54) ABSORBENT ARTICLE AND METHOD OF PRODUCTION

(75) Inventors: Anette Gustavsson, Västra Frölunda (SE); Solgun Drevik, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 836 days.

(21) Appl. No.: 10/321,538

(22) Filed: Dec. 18, 2002

(65) Prior Publication Data

US 2003/0120238 A1 Jun. 26, 2003

Related U.S. Application Data

(60) Provisional application No. 60/340,257, filed on Dec. 18, 2001.

(51) Int. Cl.
*A61F 13/15* (2006.01)
(52) U.S. Cl. .............. 604/378; 604/379; 604/380; 604/385.01
(58) Field of Classification Search .............. 604/378, 604/379, 380, 381, 383, 385.01
See application file for complete search history.

(56) References Cited

U.S. PATENT DOCUMENTS

| | | | |
|---|---|---|---|
| 3,929,135 A * | 12/1975 | Thompson | 604/385.08 |
| 3,989,867 A | 11/1976 | Sisson | |
| 3,993,820 A | 11/1976 | Repke | 428/167 |
| 4,435,178 A * | 3/1984 | Fitzgerald | 604/365 |
| 4,681,793 A | 7/1987 | Linman et al. | |
| 5,437,653 A * | 8/1995 | Gilman et al. | 604/378 |
| 5,514,120 A * | 5/1996 | Johnston et al. | 604/378 |
| 5,873,963 A | 2/1999 | Trombetta et al. | |
| 5,931,827 A | 8/1999 | Buell et al. | 604/385.29 |
| 6,187,990 B1 * | 2/2001 | Runeman et al. | 604/360 |

FOREIGN PATENT DOCUMENTS

| EP | 1 040 800 A1 | 10/2000 |
|---|---|---|
| SE | 384786 B | 5/1976 |
| WO | 99/12734 | 3/1999 |
| WO | 00/10500 | 3/2000 |

OTHER PUBLICATIONS

Derwent Abstracts of Japan, JP 2002035036-A.

* cited by examiner

*Primary Examiner*—Jacqueline F. Stephens
(74) *Attorney, Agent, or Firm*—Buchanan Ingersoll & Rooney PC (57) ABSTRACT

An absorbent article having a first liquid permeable surface layer, a essentially liquid impermeable backing layer and, located between said liquid permeable surface layer and said liquid impermeable backing layer, an absorbent body having at least one layer. The absorbent article has cavities which are essentially cone-shaped and extend at least through part of the absorbent body, said cavities having a tip part and a base, the tip part being located towards or in the liquid permeable surface layer and the base being located away from the liquid permeable surface layer. A method of production of an absorbent article with cone-shaped cavities is also provided.

20 Claims, 6 Drawing Sheets

ABSORBENT ARTICLE AND METHOD OF PRODUCTION

CROSS-REFERENCE TO RELATED APPLICATIONS

This application claims priority under 35 U.S.C. §119(e) to U.S. Provisional Application No. 60/340,257 entitled ABSORBENT ARTICLE AND METHOD OF PRODUCING IT filed on Dec. 18, 2001, the entire content of which is hereby incorporated by reference.

BACKGROUND

1. Field of the Invention

The present invention relates to an absorbent article, such as a diaper, a pant diaper, an incontinence pad, a panty liner, a micro panty liner, a sanitary towel or the like, having a first essentially liquid permeable surface layer, an essentially liquid impermeable backing layer and, located between said liquid permeable surface layer and said liquid impermeable backing layer, an absorbent body comprising at least one layer. The invention also relates to the production of such an absorbent article.

2. Related Art

When an absorbent article, such as a diaper, a pant diaper, an incontinence pad, an incontinence product with a belt, a panty liner, a micro panty liner, a sanitary towel or the like is used, part of the skin of a user is covered. This means that it is more difficult for the skin to perspire, that is to say to breathe, often with the result that it becomes warm and moist inside the absorbent article. The problem becomes even greater when the absorbent article has been used, that is to say exposed to faeces, urine, menstrual fluid, or the like.

Apart from feeling unpleasant and uncomfortable for the wearer, there are also direct hygienic aspects to be considered. A warm and moist environment can be breeding ground for bacteria, fungi and the like. This becomes particularly marked in absorbent articles which have been exposed to faeces, urine or menstrual fluid (or mixtures thereof), where a warm moist environment together with the bacterial variety which originates from the bodily discharges can lead to active growth of undesirable microorganisms with consequences such as unpleasant odors, skin irritation, rashes, itching and the like.

Attempts to bring about breathability in absorbent articles have previously been made by, inter alia, using what are known as breathable backings. EP 1,040,800 A1, for example, describes a backing layer made of plastic film with perforated holes. However, only those parts of the absorbent article which lie next to the backing layer benefit from the breathable backing and the increased airiness it is said to afford.

WO 00/10500 describes an absorbent article with what is known as a ventilation ply. The ventilation ply has large straight cylindrical holes which are intended to create breathable zones in the absorbent article. However, a large part of the absorption capacity in these parts of the core is lost. In addition, the holes are moreover occluded by other layers and therefore provide only a limited effect in the form of airiness.

OBJECTS AND SUMMARY

A need therefore exists not only to bring about breathability in part of the absorbent article but also to create a fully breathable absorbent article in a sophisticated manner, which can transport moist air away from, broadly speaking, the whole of the absorbent article while retaining leakproofness.

According to one embodiment of the present invention, an absorbent article has been produced, which article can transport moist air away from the absorbent article while retaining leakproofness. The embodiment has cavities which are essentially cone-shaped and extend at least through part of the absorbent body, and said cavities have a tip part and a base, the tip part being located towards or in the liquid permeable surface layer and the base being located away from the liquid permeable surface layer.

Essentially cone-shaped cavities are described below. In this connection, the term essentially cone-shaped cavity also means various pyramid-like and funnel-like shapes. Essentially cone-shaped cavities also means, in addition to purely conical cavities, those cavities which have more sides than a pyramidal shape. The more sides the essentially cone-shaped cavity has, the closer it comes to a pure cone shape.

By making essentially cone-shaped cavities through at least part of the absorbent body, an airy absorbent article is produced without appreciably impairing the leakage security. The absorption capacity in the ventilated absorbent body can even be regenerated to a certain extent by virtue of the liquid drying out. Such an absorbent article is very airy, that is to say breathable, because it may dry out as quickly as possible.

The liquid which the wearer discharges when wearing the article will not run down into the essentially cone-shaped cavities on account of the capillary forces in the tips of the cavities, which tips face the liquid permeable surface layer. As the cavities are essentially cone-shaped, the liquid will initially tend to remain in the tip of the cone, then being absorbed by the absorbent body and thus not running through the article.

The capillary force to which a liquid is subjected can be described approximately by Laplace's equation. Laplace's equation gives an idea of the net force which influences the liquid to go from a larger capillary to a smaller capillary:

$$\Delta P = p_A - p_R = \gamma\left(\frac{2 \cdot \cos\theta_A}{r_A} - \frac{2 \cdot \cos\theta_R}{r_R}\right) \qquad \text{Eq. 1}$$

p=the capillary force
γ=the surface tension
θ=the wetting angle
r=the radius of the capillary where the subscript A is the smaller capillary and the subscript R the larger capillary. It is therefore possible to demonstrate that the liquid will tend to not run in the direction from the tip to the wider opening of a cone-shaped cavity but will tend to stay in the tip of the essentially cone-shaped cavity. Through the base of the essentially cone-shaped cavity, air can enter into large parts of the absorbent body and in this way dry or simply air the absorbent article and thus also the skin which is covered (occluded) by the absorbent article. According to one embodiment, the essentially cone-shaped cavities extend through the whole of the absorbent body. This provides breathability and allows the absorbent article and its absorbent core to transport away moisture which might be present in the various plies of the absorbent core.

According to another embodiment, the absorbent body has essentially cone-shaped cavities arranged in specific zones of the absorbent body. In cases when extra breathability is desired in specific zones, this can be brought about by only certain parts of the absorbent article being perforated. For example, the whole article apart from the wetting zone can be perforated. In this connection, wetting zone means that part of the absorbent article which is expected to receive liquid first when, for example, urination or menstruation takes place. It is also possible to arrange the cavities in patterns such as stripes, to arrange the essentially cone-shaped cavities with different density (that is to say number of holes per unit of area) in different regions of the article, to use different sizes, for example two or more sizes, for the essentially cone-shaped cavities, or the like. It is also possible to make different zones with essentially cone-shaped cavities in combination with zones of other-shaped cavities, such as pyramid-shaped and/or funnel-shaped cavities.

In a further embodiment, a surface of the essentially cone-shaped cavities includes entirely or partly the backing layer. When the envelope surface consists entirely or partly of the backing layer, it acquires the surface characteristics of the latter. For example, it is possible with a hydrophobic backing layer to obtain a hydrophobic envelope surface which assists the essentially cone-shaped cavities in retarding or preventing passage of the essentially hydrophilic liquid through the article.

In a similar manner, it is possible to change the surface characteristics of the envelope surface in the essentially cone-shaped cavities by treating the backing layer before it is perforated and the essentially cone-shaped cavities are formed. The backing layer can also be treated during perforation itself by, for example, the roller which is used for perforation being coated with an agent which is transferred to the backing layer during perforation. In an exemplary embodiment, the inside of the essentially cone-shaped cavity is partly treated by virtue of that side of the backing layer facing away from the absorbent body coming into contact with the perforation roller.

The backing layer can also be treated on the side lying next to the absorbent body, and it is also possible to treat both sides.

Treating the backing layer may be desirable because the essentially cone-shaped cavities extend into at least part of the absorbent body and come into contact with it. The interior of the absorbent body is therefore exposed to the surface of the backing layer, and a number of possibilities are thus afforded for supplying substances or the like from the backing layer to the absorbent body. A number of possible treatments of the backing layer may be mentioned, for example pH treatment for pH control or treatment in order to provide a more hydrophobic surface. In certain cases, treatment in order to provide a less hydrophobic surface or a hydrophilic surface may be desirable. It is also possible to use an indicator treatment in order to provide an indication of various conditions such as temperature, moisture content, pH, enzyme activity or the like. The backing layer can also be treated in order to add bacteria to the article. Examples of suitable bacteria are lactobacteria, but it is also possible to carry out treatment for odor inhibition or a number of similar functions.

According to an exemplary embodiment, the envelope surface of the essentially cone-shaped cavities includes entirely or partly a separate layer, for example a plastic film or a non-woven, located between the absorbent body and the liquid impermeable backing layer. Such a layer means that the essentially cone-shaped cavities are not clearly visible from the outside, which can be psychologically important for a wearer to have confidence in the absorbent article. It also means that it is possible to give the cavities characteristics which perhaps cannot be achieved with a backing layer, or which are not desirable in a backing layer. The envelope surface of the essentially cone-shaped cavities can also be at least partly hydrophobic.

There are a number of different ways of producing a breathable absorbent article such as a diaper, a pant diaper, an incontinence pad, a panty liner, a micro panty liner, a sanitary towel or the like. For example, an exemplary production method can include:
  i) an absorbent body comprising at least one layer and having a first and a second surface is located on a backing layer with the second surface of the absorbent body towards the backing layer;
  ii) the backing layer and at least part of the absorbent body are perforated so that the backing layer and at least part of the absorbent body have cavities which are essentially cone-shaped and extend in a tapering manner from the backing layer and the second surface of the absorbent body towards the first surface of the absorbent body;
  iii) a liquid permeable surface layer is located on the first surface of the perforated absorbent body so that the absorbent body lies between the liquid permeable surface layer and the perforated backing layer, and
  iv) the liquid permeable surface layer and the backing layer are joined together.

According to an exemplary embodiment of the process, the backing layer and the absorbent body are perforated so that the backing layer and the absorbent body have cavities running all the way through. The cavities are essentially cone-shaped and extend in a tapering manner from the backing layer to the first surface of the absorbent body.

Another exemplary production method for a breathable absorbent article such as a diaper, a pant diaper, an incontinence pad, a panty liner, a micro panty liner, a sanitary towel or the like includes:
  i) an absorbent body comprising at least one layer and having a first and a second surface is located on a backing layer with the second surface of the absorbent body towards the backing layer;
  ii) a liquid permeable surface layer is located on the first surface of the absorbent body so that the absorbent body lies between the surface layer and the backing layer;
  iii) the backing layer and at least part of the absorbent body are perforated so that the backing layer and at least part of the absorbent body have cavities which are essentially cone-shaped and extend from the backing layer and the second surface of the absorbent body in a tapering manner towards the first surface of the absorbent body, and
  iv) the liquid permeable surface layer and the backing layer are joined together.

In an exemplary embodiment of the process just described, the backing layer and the absorbent body are perforated so that the backing layer and the absorbent body have cavities running all the way through. The cavities are essentially cone-shaped and extend in a tapering manner from the backing layer to the first surface of the absorbent body.

Another exemplary production method for a breathable absorbent article such as a diaper, a pant diaper, an incontinence pad, a panty liner, a micro panty liner, a sanitary towel or the like includes:
  i) an absorbent body comprising at least one layer and having a first and a second surface is perforated so that at least part of the absorbent body has cavities which are essentially cone-shaped and extend from the second surface of the absorbent body in a tapering manner towards the first surface of the absorbent body;

ii) the second surface of the absorbent body is located against a liquid impermeable backing layer;

iii) a liquid permeable surface layer is located on the first surface of the absorbent body so that the absorbent body lies between the liquid permeable surface layer and the backing layer, and iv) the liquid permeable surface layer and the backing layer are joined together.

In an exemplary embodiment of the process just described, the absorbent body is perforated so that the absorbent body has cavities running all the way through which are essentially cone-shaped. The cavities extend in a tapering manner from the second surface of the absorbent body to the first surface of the absorbent body.

Another exemplary method of producing a breathable absorbent article such as a diaper, a pant diaper, an incontinence pad, a panty liner, a micro panty liner, a sanitary towel or the like includes:

i) an absorbent body comprising at least one layer and having a first and a second surface is provided;

ii) the second surface of the absorbent body is located against a liquid impermeable backing layer;

iii) a liquid permeable surface layer is located on the first surface of the absorbent body so that the absorbent body lies between the surface layer and the backing layer, and the liquid permeable surface layer and the backing layer are joined together, and iv) the backing layer and at least part of the absorbent body are perforated so that the backing layer and at least part of the absorbent body are provided with cavities which are essentially cone-shaped and extend in a tapering manner from the backing layer and the second surface of the absorbent body towards the first surface of the absorbent body.

In the exemplary embodiment of the process just described, the backing layer and the absorbent body are perforated so that the backing layer and the absorbent body have cavities running all the way through. The cavities are essentially cone-shaped and extend in a tapering manner from the backing layer and the second surface of the absorbent body to the first surface of the absorbent body.

In all the methods just mentioned above for producing an absorbent article the perforation can be carried out by any suitable means, such as, for example, a hot-needle perforator, a cold-needle perforator, by punching, by means of tapered cutting tools, a laser, a stamp perforator, milling or the like.

BRIEF DESCRIPTION OF THE DRAWING FIGURES

The objects and advantages of the invention will become apparent from the following detailed description of preferred embodiments thereof in connection with the accompanying drawings in which like numerals designate like elements and in which.

DETAILED DESCRIPTION OF PREFERRED EMBODIMENTS

Although described herein with reference to a panty liner, the invention can be applied to a number of different absorbent articles, for example diapers, pant diapers, incontinence pads, incontinence products with a belt, panty liners, micro panty liners, sanitary towels or the like.

Figure 1:
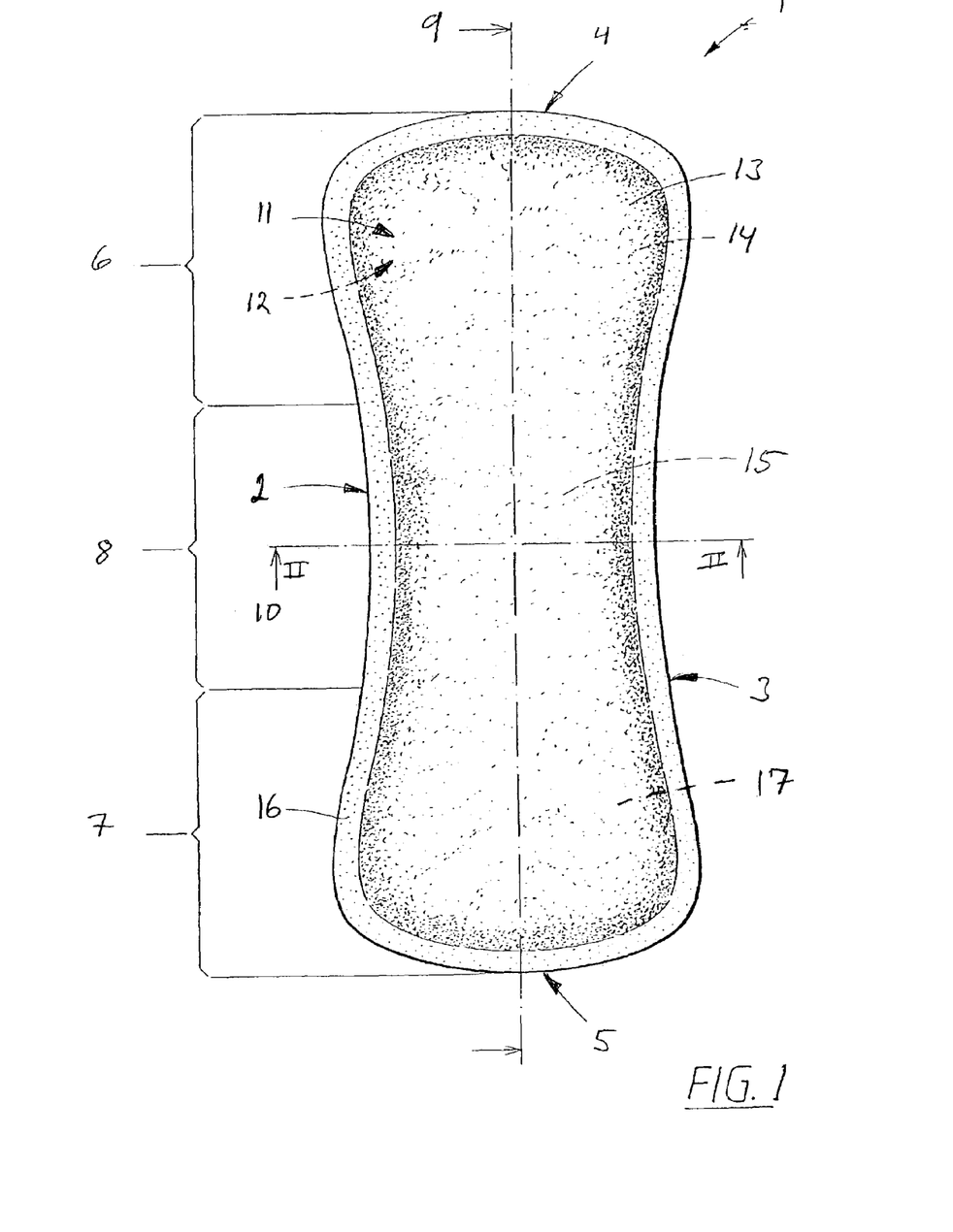
FIG. 1 shows a panty liner.
Figure 2A:
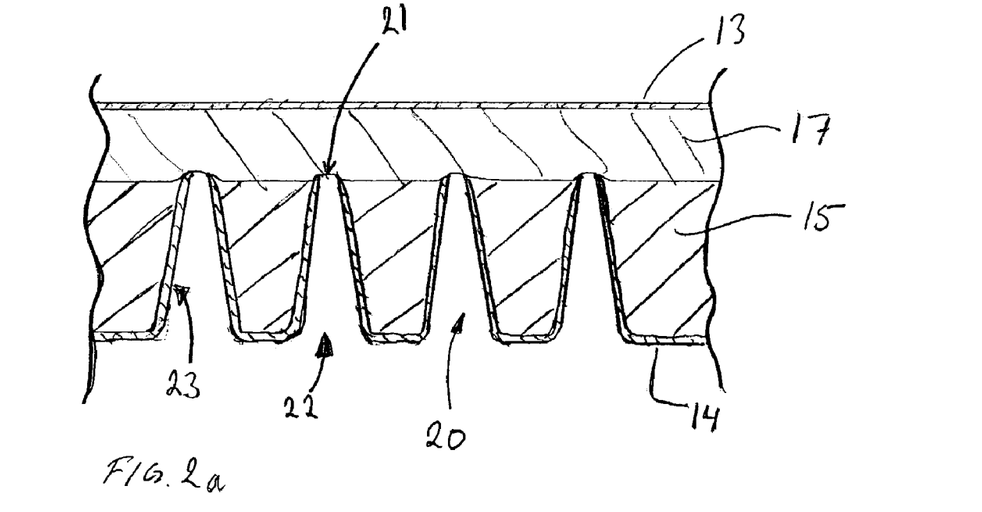
FIG. 2a shows part of a section along the line II-II through the panty liner in FIG. 1.

The exemplary panty liner 1 in FIGS. 1 and 2a has an essentially elongate shape with a longitudinal direction and a transverse direction and has two long sides 2, 3, two short sides 4, 5, a first end portion 6, a second end portion 7 and a crotch portion 8 located between the first end portion 6 and the second end portion 7, a longitudinal center line 9 extending in the longitudinal direction of the panty liner 1 and a transverse center line 10 extending in the transverse direction of the panty liner 1. Center line means a line which runs in the longitudinal or transverse direction and is located at an equal distance from the long sides 2, 3 or, respectively, the short sides 4,5 of the panty liner 1. The panty liner 1 has a top side 11 which is intended to face the wearer during use and an underside 12 intended to face away from the wearer.

The description of FIG. 1 applies to the other embodiments of FIGS. 2b-e.

The panty liner 1 comprises a liquid permeable surface layer 13 arranged on the top side 11 so that it faces the wearer during use, and a liquid-barrier backing layer 14 on the underside 12. Arranged between the surface layer 13 and the backing layer 14 is an absorbent body 15. The surface layer 13 and the backing layer 14 are suitably connected to the absorbent body 15 by, for example, adhesive and, during manufacture of the panty liner, the various layers can be pressed together, for example, during adhesive bonding by an embossed roller, the various layers can be pressed together around the edge 16 of the panty liner 1. It is also possible to emboss patterns into the article during manufacture. Inside the edge 16, the article is of essentially uniform thickness, which means that it has a plane shape in order to obtain good contact with the outer parts of the genital area of the wearer.

On the underside 12 of the panty liner 1, there may be fastening means (not shown in the figure) in the form of, for example, pressure-sensitive adhesive. The adhesive can cover the entire underside, be applied in parallel strands along the underside or be applied to the underside in another suitable pattern such as, for example, diamond patterns or dots. It is nevertheless important not to apply so much adhesive that the panty liner is no longer breathable. A removable protective layer can be arranged over the adhesive. The protective layer is removed by the wearer before fitting the panty liner in the underwear of the wearer. The protective layer can be, for example, what is known as a release paper which includes a paper layer coated with silicone, but the protective layer can also be made of another material with release characteristics, for example a packing material. It is also possible to use other fastening means, such as hook-and-loop fasteners or friction fastening.

The surface layer 13 can consist of any conventional material, for example one or more non-wovens, one or more plastic films, perforated non-woven, perforated plastic film, laminates of the materials just mentioned above or combinations thereof.

The backing layer 14 suitably includes an essentially liquid-impermeable material such as, for example, a thin liquid impermeable plastic film, or of a material which is in itself liquid permeable but has been coated with a layer of plastic, resin or some other liquid impermeable material. The backing layer 14 can therefore consist of any material which satisfies the criterion of liquid-impermeability so that leakage from the underside is prevented and has sufficient flexibility and skin-friendliness for the purpose. Examples of suitable materials are plastic films made of polyethylene, polyester or polypropylene, foams, non-wovens and laminates of non-wovens and plastic films. A backing layer which includes a laminate made of a liquid-impermeable plastic layer facing the absorbent body and a non-woven facing the underwear of the wearer provides a leakproof barrier layer with a textile feel. It is also possible to design the backing of the panty liner with a breathable backing layer made of, for example, SMS (spunbond-meltblown-spunbond non-woven) or of a breathable plastic film made of, for example, polyethylene.

An exemplary absorbent body 15 is suitably made from natural fibers such as, for example, cellulose pulp, absorbent synthetic fibers or mixtures of natural fibers and synthetic fibers. The absorbent body 15 preferably includes an airlaid cellulose body. It is also possible to mix what are known as superabsorbents into the absorbent body. A superabsorbent is a polymer which is capable of absorbing several times its own weight of liquid. The absorbent body 15 can also include additional components such as shape-stabilizers, liquid-spreading means or binders.

It is also possible to use various types of absorbent foamed material in the absorbent body. The absorbent body can of course be constructed from one or more different layers; at least one admission layer, for example, can also be included in the absorbent body. In the following figures, the absorbent body and the admission layer are described separately, but this is only to indicate a number of different embodiments which are possible within the scope of the invention and is not intended to limit the definition of absorbent body to a body without an admission layer.

An admission layer 17 is arranged between the surface layer 13 and the absorbent body 15. The admission layer 17 draws liquid into the absorbent article, spreads the liquid and transports the liquid down to the absorbent body 15. The admission layer 17 can be made of, for example, a low-density non-woven material, a wadding or the like.

FIG. 2a shows part of a section through the exemplary panty liner in FIG. 1 along the line II-II in FIG. 1. The section shows the surface layer 13, the backing layer 14 and also the admission layer 17 and the absorbent body 15. The admission layer 17 is located between the surface layer 13 and the absorbent body 15. The absorbent body 15 is located between the admission layer 17 and the backing layer 14. The panty liner 1 in FIGS. 1 and 2 has essentially cone-shaped cavities 20 which, in the embodiment shown in FIG. 2a, extend all the way through the absorbent body 15 and a little way into the admission layer 17. The essentially cone-shaped cavities 20 have a tip 21 and a base 22, the tip 21 having a smaller circumference than the base 22. According to FIG. 2a, the tip is located closer to the surface layer 13 than the base 22. The cone-shaped cavities 20 also each have an inner wall 23 or envelope surface which consists entirely or partly of the backing layer 14 which, during manufacture, helps to form the essentially cone-shaped cavities 20. The inner wall 23 also helps, after manufacture, to keep the shape of the essentially cone-shaped cavities 20. The inner wall 23 of the essentially cone-shaped cavities 20 can also entirely or partly include the absorbent body 15 in a manner not shown in the figure.

Figure 2B:
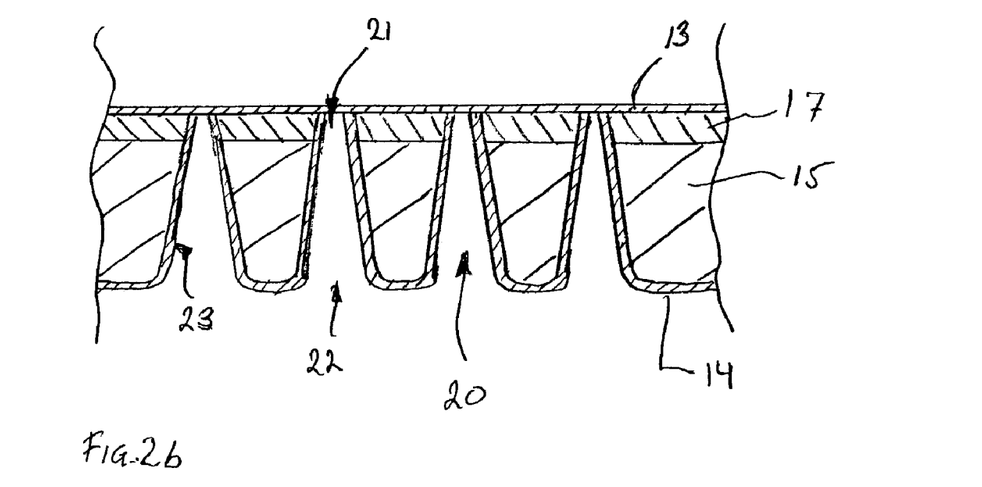
FIG. 2b shows part of a section along the line II-II through the panty liner in FIG. 1 for an alternative embodiment of the invention.

FIG. 2b shows part of a section of another exemplary embodiment. The section shows the surface layer 13, the backing layer 14 and also the admission layer 17 and the absorbent body 15. The admission layer 17 is located between the surface layer 13 and the absorbent body 15. The absorbent body 15 is located between the admission layer 17 and the backing layer 14. The panty liner in FIG. 2b has essentially cone-shaped cavities 20 which, in this embodiment, extend all the way through the absorbent body 15 and all the way through the admission layer 17. The essentially cone-shaped cavities 20 have a tip 21 and a base 22, the cavity having a smaller circumference at the tip 21 than at the base 22. In FIG. 2b, the tip 21 is located closer to the surface layer 13 than the base 22. The cone-shaped cavities 20 also each have an inner wall 23 which entirely includes the backing layer 14.

Figure 2C:
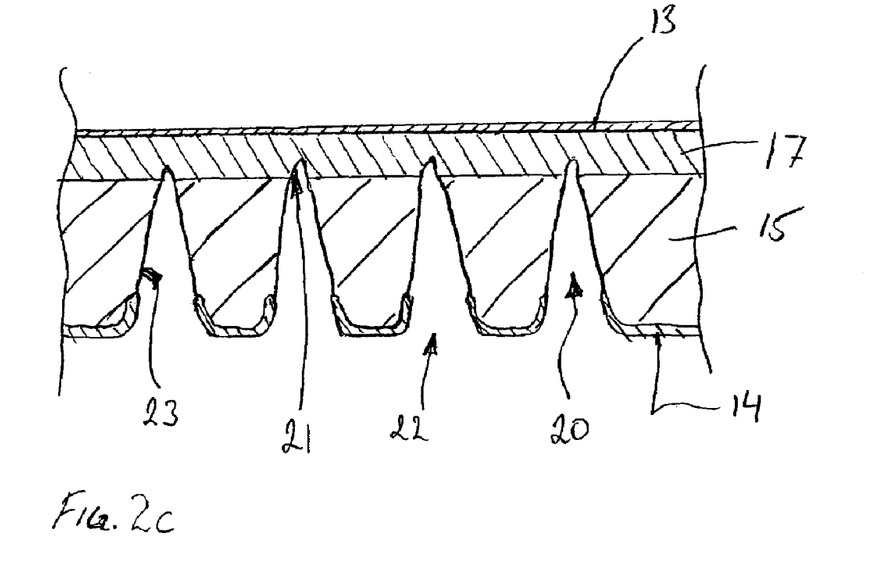
FIG. 2c shows part of a section along the line II-II through the panty liner in FIG. 1 for an alternative embodiment of the invention.

FIG. 2c shows part of a section of a further exemplary embodiment of a panty liner. The section shows the surface layer 13, the backing layer 14 and also the admission layer 17 and the absorbent body 15. The admission layer 17 is located between the surface layer 13 and the absorbent body 15. The absorbent body 15 is located between the admission layer 17 and the backing layer 14. The panty liner in FIG. 2c has essentially cone-shaped cavities 20 which, in this embodiment, extend all the way through the absorbent body 15 and part of the way through the admission layer 17. The essentially cone-shaped cavities 20 have a tip 21 and a base 22, the circumference of the cavities being smaller at the tip 21 than at the base 22. The cone-shaped cavities 20 also each have an inner wall 23 or envelope surface which partly includes the backing layer 14 and also of the absorbent body 15 and to a certain extent the admission layer 17.

Figure 2D:
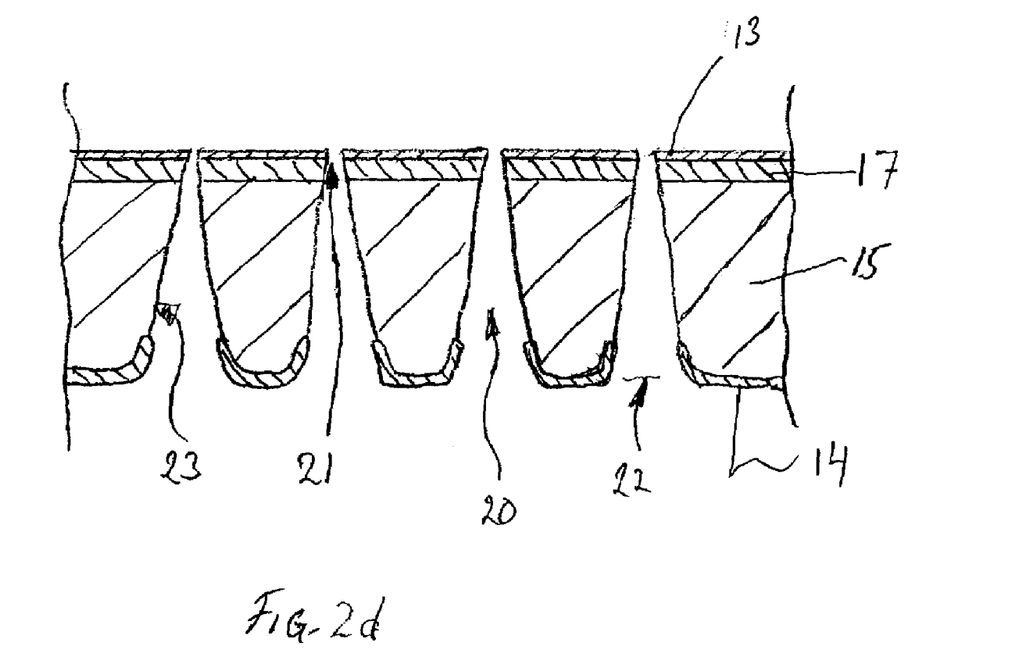
FIG. 2d shows part of a section along the line II-II through the panty liner in FIG. 1 for an alternative embodiment of the invention.

FIG. 2d shows part of a section of a further exemplary embodiment of a panty liner. The section shows the surface layer 13, the backing layer 14 and also the admission layer 17 and the absorbent body 15. The admission layer 17 is located between the surface layer 13 and the absorbent body 15. The absorbent body 15 is located between the admission layer 17 and the backing layer 14. The panty liner in FIG. 2d has essentially cone-shaped cavities 20 which, in this embodiment, extend all the way through the absorbent body 15 and all the way through the admission layer 17 and also through the surface layer 13. The essentially cone-shaped cavities 20 have a tip 21 and a base 22, the circumference of the cavities 20 being smaller at the tip 21 than at the base 22. The cone-shaped cavities 20 also each have an inner wall 23 or envelope surface which partly include the backing layer 14 and also of the absorbent body and to a certain extent the admission layer 17 and the surface layer 13.

Figure 2E:
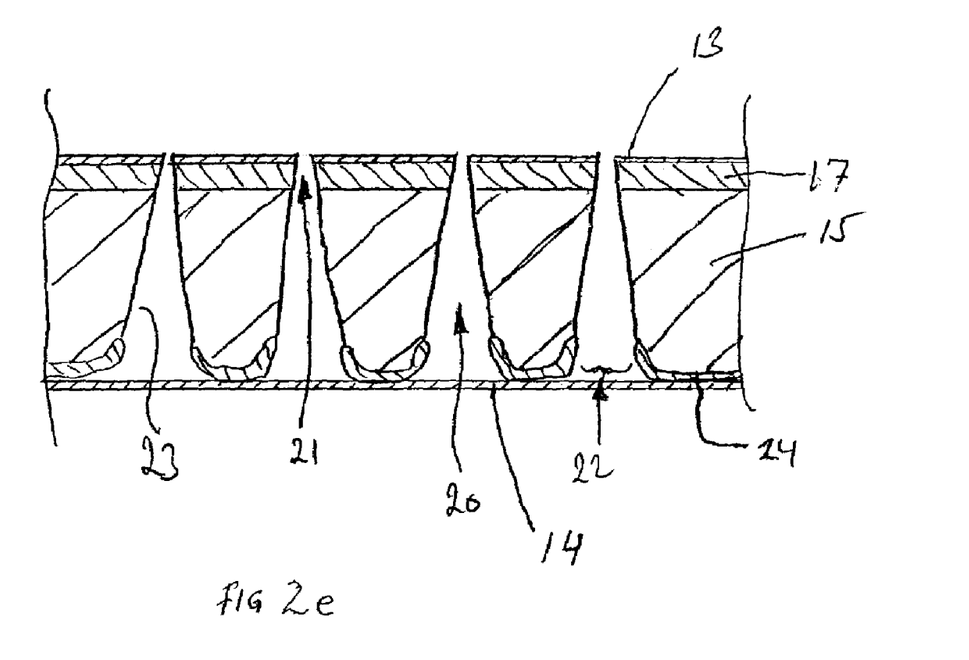
FIG. 2e shows part of a section along the line II-II through the panty liner in FIG. 1 for an alternative embodiment of the invention.

FIG. 2e shows part of a section of a further exemplary embodiment of a panty liner. The section shows the surface layer 13, a first backing layer 24 and also the admission layer 17 and the absorbent body 15. The admission layer 17 is located between the surface layer 13 and the absorbent body 15. The absorbent body 15 is located between the admission layer 17 and the first backing layer 24. The panty liner in FIG. 2e also has essentially cone-shaped cavities 20 which, in this embodiment, extend all the way through the absorbent body 15 and all the way through the admission layer 17 and also through the surface layer 13. The essentially cone-shaped cavities 20 have a tip 21 and a base 22, the tip 21 being smaller than the base 22. The cone-shaped cavities 20 also each have an inner wall 23 or envelope surface which partly includes the first backing layer 24 and also of the absorbent body and to a certain extent the admission layer 17 and the surface layer 13. The panty liner in FIG. 2e also has a second, outer backing layer 14 which is located against the first backing layer 24 so that the essentially cone-shaped cavities 20 are not visible, or are not immediately conspicuous. The first backing layer 24 and the second backing layer 14 can include the same material but can also include different materials. Preferably, at least the second backing layer 14 is made of an essentially breathable material.

Figure 3A:
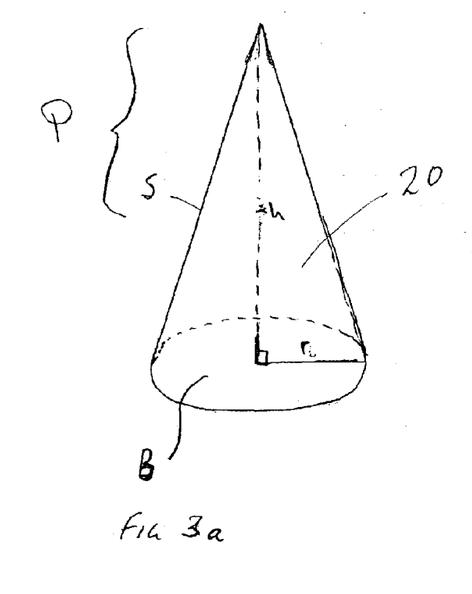
FIGS. 3a-b show essentially cone-shaped volumes.

It is possible to describe the essentially cone-shaped cavity 20 using, for example, an ordinary cone according to FIG. 3a with a height h, a base radius r, a side s, a base area $B=\pi \cdot r^2$, an envelope surface $M=\pi \cdot r \cdot s$ and a volume $V=(\pi \cdot r^2 \cdot h)/3$, and also a tip part P.

Figure 3B:
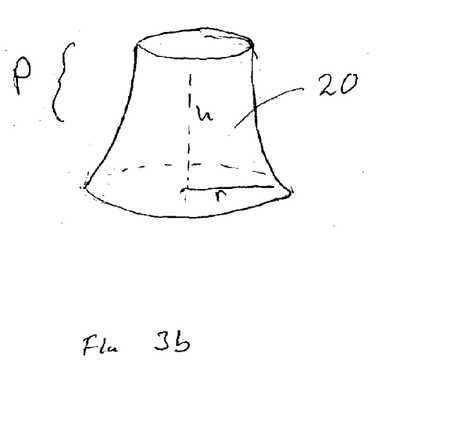

FIG. 3b shows an alternative embodiment of an essentially cone-shaped cavity. The tip part P is blunted and has a flat surface opposite the base. This shape is of course applicable to pyramid-shaped cavities.

Figure 3C:
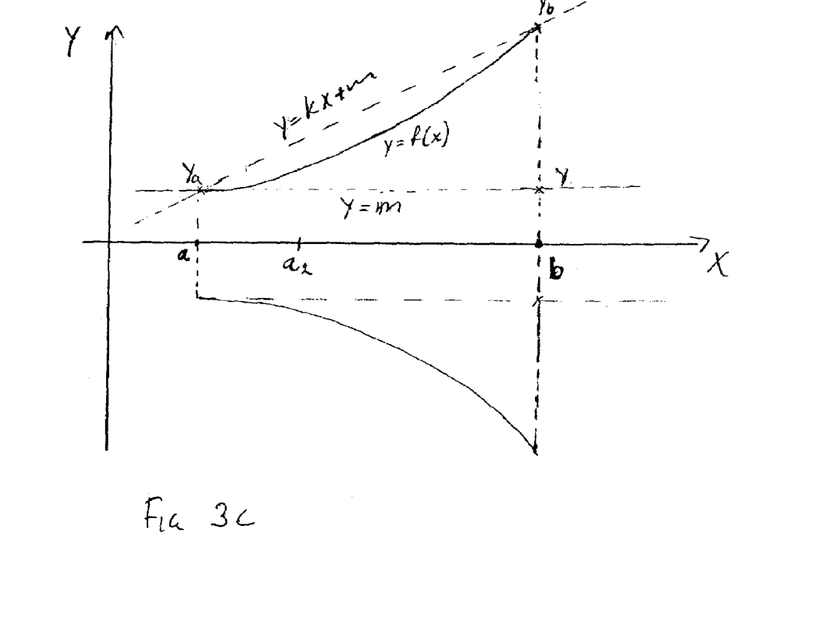
FIG. 3c shows an X-Y diagram in which a rotation function with associated delimitations is plotted.

According to another embodiment, it is possible to describe all or part of the essentially cone-shaped hole by rotating a function f(X) around the X axis in an X-Y diagram as shown in FIG. 3c. The volume V is then obtained by the formula:

$$V = \int_a^b \pi \cdot Y^2 \cdot dX = \pi \int_a^b f^2(X) \cdot dX \qquad \text{Eq. 2}$$

This applies when $Y_a<Y_b$, that is to say when $f(X_a)<f(X_b)$, that is to say the value Y of the function at the point a should be less than the value Y of the function at the point b, and also $a \leq a_2 < b$.

In addition to this, the function Y=f(X) which describes the essentially cone-shaped hole can be such that values for Y are $Y \leq kX+m$ in the interval X=a and X=b, and also the function Y=f(X) can be such that values for Y are Y>m in the interval X=a and X=b, where a defines the tip and b the base of the cone.

Where Y=kX+m is the equation of the straight line, k is the inclination of the line and m is the intersection with the Y axis when X=0. On rotation of Y=kX+m in the interval X=a and X=b and with a<b and m=0, the ordinary cone shown in FIG. 3a is described.

According to another exemplary embodiment, the essentially cone-shaped hole can have a more funnel-like shape. The essentially cone-shaped hole is then described by values for Y of Y=m in the interval X=a and $X=a_2$, and the remaining part is described by the function Y=f(X) having values for Y of Y<kX+m in the interval $X=a_2$ and X=b and the function Y=f(X) having values for Y of Y>m in the interval $X=a_2$ and X=b and $a<a_2<b$.

It should be noted that the Y axis corresponds to the longitudinal and transverse planes of the absorbent article and that the X axis corresponds to the thickness of the absorbent article, that is to say the distance between the liquid permeable surface layer and the essentially liquid impermeable backing layer of the absorbent article.

In one embodiment, the cavities have a height of roughly 0.5-30 millimeters, preferably 0.5-5 mm. The essentially cone-shaped cavities can have a base radius of roughly 0.5-10 mm, preferably 0.5-5 mm, and most preferably 0.5-2 mm.

In some exemplary embodiments, it may be advantageous to describe the base area instead of a radius, especially when a pyramid or a funnel-like cavity is described. The base area of the cavities is then roughly 0.78-315 mm², preferably 0.78-79 mm², and most preferably 0.78-51 mm².

EXAMPLE

An exemplary panty liner was manufactured with the following construction, in order: a surface layer made of carded non-woven with a basis weight of 26 g/m². The surface layer was attached using a hot-melt adhesive with a basis weight of 7 g/m² to a distribution ply in the form of an airlaid non-woven paper with a basis weight of 80 g/m² which was in turn attached using a hot-melt adhesive with a basis weight of 9 g/m² to an absorbent body made of chemithermomechanical pulp (CTMP) with a basis weight of 200 g/m². Superabsorbents (SAPs) with a basis weight of 50 g/m² were mixed into the absorbent body. The absorbent body was attached using a hot-melt adhesive with a basis weight of 5 g/m² to a polypropylene non-woven with a basis weight of 30 g/m².

The entire article was cold-needle-perforated in order to produce essentially cone-shaped cavities. A layer of spunbond non-woven with a basis weight of 22 g/m² was then applied as backing layer. A hot-melt adhesive with a basis weight of 35 g/m² was subsequently applied to the backing layer, after which a release paper (protective paper for the fastening adhesive) with a basis weight of 43 g/m² was applied over the adhesive.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. An absorbent article comprising:
   a first liquid permeable surface layer;
   a substantially liquid impermeable backing layer; and
   an absorbent body located between the liquid permeable surface layer and the substantially liquid impermeable backing layer, the absorbent body including at least one layer,
   wherein the absorbent article includes at least one cavity which is substantially cone-shaped and extends at least through part of the absorbent body, the cavity having a tip part and a base, the tip part being located toward or in the liquid permeable surface layer and the base being located away from the liquid permeable surface layer, wherein the smallest cross section of the cavity is located closer to the liquid permeable surface layer than is the largest cross section of the cavity.

2. The absorbent article according to claim 1, wherein the at least one cavity extends through the whole of the absorbent body.

3. The absorbent article according to claim 1, wherein the absorbent body has a plurality of cavities in specific zones.

4. The absorbent article according to claim 1, wherein the absorbent body has a plurality of cavities of different sizes.

5. The absorbent article according to claim 1, wherein an envelope surface of the at least one cavity is formed entirely or partly from the backing layer.

6. The absorbent article according to claim 5, wherein the envelope surface of the cavities is at least partly hydrophobic.

7. The absorbent article according to claim 1, wherein an envelope surface of the at least one cavity is formed entirely or partly of a separate layer located between the absorbent body and the substantially liquid impermeable backing layer.

8. The absorbent article according to claim 7, wherein the envelope surface of the cavities is at least partly hydrophobic.

9. The absorbent article according to claim 1, wherein an envelope surface of the at least one cavity is formed entirely or partly of a plastic film located between the absorbent body and the substantially liquid impermeable backing layer.

10. The absorbent article according to claim 9, wherein the envelope surface of the cavities is at least partly hydrophobic.

11. The absorbent article according to claim 1, wherein the backing layer includes one or more agents selected from the group consisting of pH control agent, a hydrophobic agent to provide a less hydrophobic surface of a hydrophilic surface, and an odor inhibition agent.

12. The absorbent article according to claim 1, wherein the backing layer includes one or more indicating agents to indicate a parameter selected from the group consisting of temperature, moisture content, pH, and enzyme activity.

13. The absorbent article according to claim 1, wherein the backing layer includes a bacteria.

14. The absorbent article according to claim 13, wherein the bacteria is lactobacteria.

15. The absorbent article according to claim 1, wherein the at least one cavity has a height of 0.5-30 mm and a base area of 0.19-79 $mm^2$.

16. The absorbent article according to claim 15, wherein the height is 0.5-5 mm.

17. The absorbent article according to claim 15, wherein the base area is 0.19-40 $mm^2$.

18. The absorbent article according to claim 17, wherein the base area is 0.19-4 $mm^2$.

19. The absorbent article according to claim 1, wherein a volume of the at least one cavity is described by rotating a first function Y=f(X) around the X axis in an X-Y diagram, the volume V being obtained by the formula:

$$V = \int_a^b \pi \cdot Y^2 \cdot dX = \pi \int_a^b f^2(X) \cdot dX, \text{ where } a < b$$

wherein the first function Y=f(X) has a value for Y of $\leq$ Y (kX+m) in a first interval X=a and X=b, and Y>m in a second interval X=a and X=b, where a defines the tip part and b the base of the cavity, and wherein Y=(kX+m) is an equation of a straight line, where k is an inclination of the straight line and m is an intersection of the straight line with the Y axis when X=0.

20. The absorbent article according to claim 1 wherein the at least one cavity is spaced from an outer surface of the liquid permeable surface layer.

* * * * *